US010215753B2

(12) United States Patent
Miller et al.

(10) Patent No.: US 10,215,753 B2
(45) Date of Patent: Feb. 26, 2019

(54) METHOD FOR THE TOPOGRAPHICALLY-SELECTIVE PASSIVATION OF MICRO- AND NANOSCALE DEVICES

(71) Applicants: Benjamin L. Miller, Penfield, NY (US); Mark A. Lifson, Rochester, NY (US); Dhruba Jyoti Basu Roy, Rochester, NY (US)

(72) Inventors: Benjamin L. Miller, Penfield, NY (US); Mark A. Lifson, Rochester, NY (US); Dhruba Jyoti Basu Roy, Rochester, NY (US)

(73) Assignee: University of Rochester, Rochester, NY (US)

( * ) Notice: Subject to any disclaimer, the term of this patent is extended or adjusted under 35 U.S.C. 154(b) by 802 days.

(21) Appl. No.: 14/452,141

(22) Filed: Aug. 5, 2014

(65) Prior Publication Data
US 2015/0037815 A1 Feb. 5, 2015

Related U.S. Application Data

(60) Provisional application No. 61/862,374, filed on Aug. 5, 2013.

(51) Int. Cl.
*G01N 21/75* (2006.01)
*G01N 21/77* (2006.01)
*G01N 33/543* (2006.01)

(52) U.S. Cl.
CPC ....... *G01N 33/54393* (2013.01); *G01N 21/77* (2013.01); *G01N 33/54373* (2013.01); *G01N 2021/757* (2013.01); *G01N 2021/7773* (2013.01); *G01N 2021/7776* (2013.01); *G01N 2021/7783* (2013.01); *G01N 2021/7789* (2013.01)

(58) Field of Classification Search
CPC ............. G01N 21/77; G01N 33/54373; G01N 33/54393; G01N 2021/757; G01N 2021/7773; G01N 2021/7776; G01N 2021/7783; G01N 2021/7789
See application file for complete search history.

(56) References Cited

U.S. PATENT DOCUMENTS 6,103,033 A * 8/2000 Say ................... A61B 5/14532
156/238
6,180,288 B1 * 1/2001 Everhart .......... G01N 33/54373
264/1.1

(Continued)

OTHER PUBLICATIONS

Eftekhari et al., "Nanoholes as Nanochannels: Flow-through Plasmonic Sensing," Anal. Chem. 81:4308-4311 (2009).

*Primary Examiner* — Scott Long
*Assistant Examiner* — Gary E Hollinden
(74) *Attorney, Agent, or Firm* — LeClairRyan PLLC (57) ABSTRACT

Disclosed is a method of preparing a biosensor that involves providing a substrate including a surface having a topographical pattern formed at one or more sites on or in the surface, coating the substrate with a solution including hydrogel particles, wherein the hydrogel particles self-assemble on the surface to mask the surface except at the one or more sites, and binding one or more capture molecules to the one or more sites to form the biosensor. Systems that include the biosensor, as well as methods of using the biosensor, are also disclosed.

13 Claims, 4 Drawing Sheets

(56) References Cited

U.S. PATENT DOCUMENTS

| | | | |
|---|---|---|---|
| 6,391,937 B1* | 5/2002 | Beuhler | C08F 8/00 |
| | | | 428/474.4 |
| 7,226,733 B2 | 6/2007 | Chan et al. | |
| 7,292,349 B2 | 11/2007 | Miller et al. | |
| 9,678,068 B2* | 6/2017 | Duffy | G01N 33/54393 |
| 9,791,439 B2* | 10/2017 | Vivien | G01N 33/54386 |
| 9,823,210 B2* | 11/2017 | Di Matteo | G01N 27/28 |
| 9,869,616 B2* | 1/2018 | Kim | G01N 33/5436 |
| 9,921,165 B2* | 3/2018 | Bailey | C12Q 1/6804 |
| 2003/0112443 A1* | 6/2003 | Hjelme | G01N 21/45 |
| | | | 356/480 |
| 2006/0040274 A1* | 2/2006 | Tsinberg | B01J 19/0046 |
| | | | 435/6.19 |
| 2009/0041825 A1* | 2/2009 | Kotov | C12M 21/08 |
| | | | 424/423 |
| 2010/0112707 A1* | 5/2010 | Kansakoski | G01N 33/54373 |
| | | | 436/86 |
| 2010/0279886 A1 | 11/2010 | Fauchet et al. | |
| 2014/0017772 A1* | 1/2014 | Di Matteo | C12Q 1/001 |
| | | | 435/287.1 |
| 2014/0242632 A1* | 8/2014 | Kim | G01N 33/5436 |
| | | | 435/29 |
| 2014/0342394 A1* | 11/2014 | Parker | G01N 33/5088 |
| | | | 435/30 |

* cited by examiner

METHOD FOR THE TOPOGRAPHICALLY-SELECTIVE PASSIVATION OF MICRO- AND NANOSCALE DEVICES

This application claims the benefit of U.S. Provisional Patent Application Ser. No. 61/862,374, filed Aug. 5, 2013, which is hereby incorporated by reference in its entirety.

This invention was made with government support under 5RO1 AI080770 awarded by the National Institutes of Health. The government has certain rights in the invention.

TECHNOLOGICAL FIELD

This application relates to a method for the topographically-selective passivation of micro- and nanoscale devices, the resulting devices formed thereby, and biological sensors containing the same.

BACKGROUND

The detection of biomedically significant molecules with high-sensitivity nanoscale optical sensors has been the focus of major development efforts by many research groups worldwide (Fan et al., *Anal. Chim. Acta* 620:8-26 (2008)). Novel structures resulting from these efforts, including ring- and whispering-gallery resonators (Chao et al., *Appl. Phys. Lett.* 83:1527-1529 (2003); Armani et al., *Science* 317:783-787 (2007); Barrios et al., *Opt. Lett.* 32:3080-3082 (2007)), waveguides (Heideman et al., *Sens. Actuators* 10:209-217 (1993); Goddard et al., *Analyst* 119:583-588 (1994); Salamon et al., *Biophys. J.* 80:1557-1567 (2001)), and photonic crystals (Vollmer et al., *Appl. Phys. Lett.* 80:4057-4059 (2002); Krioukov et al., *Opt. Lett.* 27:1504-1506 (2002)), operate by resolving minute changes in refractive index that occur when a target molecule or virus interacts with the device. While all of these devices have remarkable theoretical sensitivities, their observed limits of detection ("LoD") under real-world conditions are often unsatisfactory (Fan et al., *Anal. Chim. Acta* 620:8-26 (2008); Sheehan et al., *Nano Lett.* 5:803-807 (2005).

The LoD of a biosensor is dependent not only on the sensitivity of the transduction mechanism, but also on the biomolecular thermodynamics of the immobilized probe and the target analyte in solution (Lambeck, *Meas. Sci. Technol.* 17:R93-R116 (2006); Kusnezow et al., *Mol. Cell. Proteomics* 5:1681-1696 (2006)). In addition to presenting unique challenges for analyte mass transport, nanoscale sensors require careful functionalization with capture molecules (for example, antibodies) since the active sensing region is orders of magnitude smaller than the overall device. If the placement of capture molecules (probes) onto the surface is indiscriminate and both the sensing and non-sensing regions are functionalized (Sapsford et al., *Anal. Chem.* 73:5518-5524 (2001); Choi et al., *Anal. Biochem.* 405:1-10 (2010)), the target loss to the non-sensing regions may become substantial enough to disturb the bulk concentration of target. This can lead to a lower fraction of material being bound to the sensing area, and a higher (worse) LoD (Ekins et al., *Clin. Chem.* 37:1955-1967 (1991); Ekins, *Clin. Chem.* 44:2015-2030 (1998); Parpia et al., *Anal. Biochem.* 401:1- (2010)). Conventional passivation techniques (Taylor et al., *Nucleic Acids Res.* 31:e87 (2003)) involving incubation with proteins (e.g. bovine serum albumin) or synthetic blocking chemicals cannot be used to avoid this issue, since they would result in equal application to the non-sensing and sensing areas of nanoscale devices. A common top-down approach to this problem has been to shrink the size of the probe droplet in manufacturing to closely overlay only the active sensing region (McKendry et al., *Proc. Natl. Acad. Sci. U.S.A.* 99:9783-9788 (2002); Lee et al., *Nano Lett.* 4:1869-1872 (2004)). However, there are considerable challenges with alignment and uniform dispensing on such a small scale. Others have exploited material differences within a nanoscale biosensor. For example, Fuez et al. showed material-selective surface chemistry that selectively bound a blocking agent to inactive titanium dioxide surfaces of a plasmonic nanostructure leaving the gold sensing region to bind biomolecules (Feuz et al., *ACS Nano* 4:2167-2177 (2010)). Since incorporation of different materials into the device is not always feasible, alternative strategies are clearly needed.

The devices and methods disclosed herein are directed to overcoming these and other deficiencies in the art.

SUMMARY

A first aspect relates to a method of preparing a biosensor that includes providing a substrate including a surface having a topographical pattern formed at one or more sites on or in the surface, coating the substrate with a solution comprising hydrogel particles, wherein the hydrogel particles self-assemble on the surface to mask the surface except at the one or more sites, and binding one or more capture molecules to the one or more sites to form the biosensor.

A second aspect relates to a biosensor prepared according to the method described above.

A third aspect relates to a biosensor that includes a substrate including a surface having a topographical pattern formed at one or more sites on or in the surface, and one or more capture molecules bound to the one or more sites to form the biosensor, the one or more capture molecules binding specifically to a target molecule under suitable conditions, wherein at least 80 percent of one or more types of capture molecules bound to the surface of the substrate are bound at the one or more sites.

A fourth aspect relates to a method of detecting the presence of a target molecule in a sample that includes providing a biosensor as described above, exposing a sample to the one or more sites on the biosensor surface, and detecting a change in an optical property of the biosensor at the one or more sites following the exposing.

A fifth aspect relates to a system that includes a biosensor as described above, a light source coupled to the biosensor to pass light into or across the topographical pattern, and a detector coupled to the biosensor to detect light passing from or across the topographical pattern.

A sixth aspect relates to a method of quantifying the amount of a biological target present in a sample that includes providing a biosensor as described above, exposing a sample to the one or more sites on the biosensor surface, and detecting a change in an optical property of biosensor surface at the one or more sites following the exposing, wherein the amount of biological target is quantifiable based on the extent of the change of the optical property.

Nanoscale biosensors have remarkable theoretical sensitivities, but often suffer from sub-optimal limits of detection in practice. This is in part because the sensing area of nanoscale sensors is orders of magnitude smaller than the total device substrate. Current strategies to immobilize probes (capture molecules) functionalize both the sensing and non-sensing regions, leading to target depletion and diminished limits of detection. The difference in topography between these regions on nanoscale biosensors offers a way to selectively address only the sensing area. A bottom-up, topographically selective approach employing self-assembled hydrogel nanoparticles as a mask to preferentially bind target to the active sensing region of a biosensor has been developed using a photonic crystal (PhC) as a proof of concept. This led to over one order of magnitude improvement in the limit of detection for the device, in agreement with finite element simulations. Since the sensing elements in many nanoscale sensors are topographically distinct, as in the PhC biosensor, this approach should be widely applicable.

BRIEF DESCRIPTION OF THE DRAWINGS

FIG. 3B high very sensitive as a surface of the ring is scanned by an evanescent field of a light wave propagating within the ring. Currently, ring resonators are used to perform measurements with a selectively working absorber surface, which is labeled with one or more capture molecules and therefore plays an important role for an adequate specificity of the sensor. The capture of a targeted bio-molecule at the working surface cause an optical ring circumference to vary. Thus, an effective refractive index of the ring resonator changes upon capture of the targeted bio-molecule such that wavelengths of resonant modes are shifted. The detection of the shift into a coupled detection waveguide can indicate presence of the bio-molecule. When utilized in the devices and methods described herein, the hydrogel particles are used to mask regions of the ring resonator substrate other than where the working absorber surface resides.

Ultrahigh-Q silica toroidal microcavities are particularly attractive for use in applications of biomolecular sensing because they can be fabricated on a chip. The toroidal microcavity can have any desired configuration, e.g., ring, ellipsoidal, or polygonal configurations. In one approach, an $SiO_2$ disk cavity can be fabricated on a silicon wafer by, e.g., thermal dioxidation, photolithography, and $SiO_2$ etching. The dioxide layer can be on the micron or submicron level. Next, the silicon sacrificial layer is undercut to form a Si post. With a combination of isotropic and anisotropic etching, a silicon post can be obtained and then the $SiO_2$ is exposed with a laser suitable to transfer the shape of the silicon post to the $SiO_2$ and form a smooth toroidal cavity of the desired configuration. As an alternative to $SiO_2$, other oxide glasses can be used to form the toroidal microcavity. The toroidal microcavity may have any suitable arrangement between the microcavity and working waveguide surfaces, including single or multiple microcavity constructions. Toroidal microcavities are useful to increase the distance between adjacent resonance wavelengths. One suitable structure of the microcavity sensor is illustrated in U.S. Application Publ. No. US20090097031 A1 to Armani et al., the disclosure of which is incorporated herein by reference in its entirety. One example for use of toroidal microcavities in a biosensor is described in U.S. Patent Publication No. 20090093375 to Arnold et al., the disclosure of which is incorporated herein by reference in its entirety. When utilized in the devices and methods described herein, the hydrogel particles are used to mask regions of the toroidal microcavity substrate other than where the microcavity is formed. This can facilitate coupling of the capture molecules to the microcavity surface.

A waveguide is a structure which guides optical waves by total internal reflection (TIR). When a light beam traveling in a waveguide is totally internally reflected at the interface between the waveguide and an adjacent medium having a lower refractive index, a portion of the electromagnetic field of the TIR light penetrates shallowly into the adjacent medium. The use of waveguides in the design of biosensors has been described in numerous publications including U.S. Pat. No. 5,814,565 to Reichert et al., the disclosure of which is incorporated herein by reference in its entirety. The waveguide can be fabricated on a substrate surface, in which case the hydrogel particles are used to mask regions of the substrate other than where the waveguide is formed.

Alternatively, a waveguide can be formed within a recessed region of the substrate so as to form trenches on either side of the waveguide. With this configuration, hydrogel particles mask regions on either side of the trenches leaving the waveguide exposed.

Photonic bandgap structures allow light within certain well-defined wavelength bands to be guided without a total internal reflection mechanism. Photonic band gap structures are configured so as to confine and guide light through resonant reflections, and do not depend on total internal reflections. Accordingly, much greater flexibility is allowed in the design and construction of such structures.

Photonic band gap structures may be fabricated by machining blocks of dielectric material, although other methods of fabricating photonic band gap structures may involve the mechanical drilling or machining of holes or cavities in solid blocks of a dielectric material. Another method may involve the use of chemical removal, such as reactive ion etching, to fabricate holes or cavities in solid blocks of dielectric material. Alternatively, photonic band gap structures may be fabricated by stacking a collection of dielectric elements in a desired pattern. Where the photonic band gap structure is formed in a block of solid material by forming holes or cavities, the hydrogel particles are used to mask regions of the substrate other than where the holes or cavities are formed. Where the photonic band gap structure is formed in a block of solid material by forming holes or cavities, the hydrogel particles are used to mask regions of the substrate other than where the holes or cavities are formed.

A Bragg reflector is a sensor element utilizing more than one layer of materials with varying refractive indexes that result in detection of a reflectivity shift having one or more sharply defined luminescent peaks. A biosensor comprising a Bragg reflector is described in U.S. Pat. No. 7,226,733 to Chan et al., the disclosure of which is incorporated herein by reference in its entirety. The periodicity and design of the upper and lower Bragg reflectors can have any suitable configuration. When used with macroporous or mesoporous Bragg structures, it is possible to confine capture molecule location to the pores of the Bragg structures. Confinement to the pores rather that the outer surface of the Bragg structure can be achieved by masking the outer surfaces with the hydrogel particles prior to capture molecule coupling.

A diffraction grating operates at a fixed wavelength and detection angle by exploiting the variation in diffraction efficiency that occurs due to the presence of a chemical or biological species on a diffraction grating. Any of a variety of suitable diffraction grating structures (channel depth, width, and spacing) can be employed. In traditional diffraction-based biosensors, chemical or biological species are selectively adsorbed onto the top surface of a diffraction grating, giving rise to an increase in the diffraction efficiency proportional to the change in the grating thickness. One exemplary diffraction grating based sensor is described in U.S. Pat. No. 8,349,617 to Weiss et al., the disclosure of which is incorporated herein by reference in its entirety. In addition, surface-plasmon enhancement can be enhanced by nanoparticles (Wark et al., "Nanoparticle-Enhanced Diffraction Gratings for Ultrasensitive Surface Plasmon Biosensing," *Anal. Chem.* 79:6697-6701 (2007), the disclosure of which is incorporated herein by reference in its entirety). In the devices and methods described herein, the hydrogel particles can be used to mask regions of the device that lack diffraction grating structures.

A plasmonic waveguide involves excitations which do not exhibit the disadvantages associated with using light sources to determine a specific binding event. These surface plasmon polaritons or plasmonic mode excitations, i.e., electromagnetic excitations at a metal-dielectric interface, may be guided using structures that are much smaller than the wavelength of photons of the same frequency. Any of a variety of SPR-biosensor structures can be utilized in forming a biosensor. These structures can be provided with any of a variety of topographical structures on the sensing surface. One exemplary plasmonic waveguide is described in U.S. Pat. No. 6,373,577 to Bräuer et al., the disclosure of which is incorporated herein by reference in its entirety. Where the SPR-based sensor structure includes grating patterns, or holes or cavities in which capture molecules are intended to reside, the hydrogel particles are used to mask the outer surface of the substrate other than where the grating, holes or cavities are formed. Where the SPR-based sensor structure includes raised structures intended to contain the capture molecules, the hydrogel particles are used to mask regions of the substrate other than where the raised structures are formed.

Glass-supported gold nanostructure dimers include a pair of the nanostructures supported on a glass substrate and separated from one another by a nanogap on the order of about 1 to about 10 nm. The gold nanostructures include, without limitation, disks, bowties, nanorods, and rings, which can have any suitable dimension. Light passes through the nanogap, and polarization of longitudinal and transverse polarizations are obtained. As the gold dimers approach each other, an exponential red shift and slight blue shift of coupled bonding mode is obtained for these polarizations. Near-field coupling in gold dimers causes an exponential increase in sensitivity to refractive index of surrounding medium with decreasing the gap distance. Thus, capture of the target molecule at the gap interface will induce a change in the refractive index and a shift in the coupled bonding modes. Exemplary gold dimers are described in Tsai et al., "Plasmonic Coupling in Gold Nanoring Dimers: Observation of Coupled Bonding Mode," *Nano Lett.* 12(3):1648-54 (2012); Tanaka et al., "Nanoscale Interference Patterns of Gap-mode Multipolar Plasmonic Fields," *Scientific Reports* 2(764):doi:10.1038/srep00764 (2012); and Ye et al., "Plasmonic Behaviors of Gold Dimers Perturbed by a Single Nanoparticle in the Gap," *Nanoscale* 4(22):7205-11 (2012), the disclosures of which are incorporated herein by reference in their entirety. Because the dimer paired nanostructures are supported on the surface of a substrate, hydrogel particles can be used to mask regions of the substrate so as to confine capture molecule binding to only the raised nanostructure pairs.

Nanoplasmonic pores have the advantage of exhibiting unique optical transmission characteristics at resonant wavelengths. Any sensor structure comprising nanoplasmonic pores can be used in the present invention. The nanopores are formed in a submicron membrane including a metal film (e.g., gold, silver, platinum). The nanopores can be dimensioned to facilitate maximal response in consideration of the target molecule, but typically the nanopores are on the order of less than 250 nm, preferably less than 150 nm in diameter. Capture molecules bound within the nanopore features allow for specific binding of the target molecule within the nanopore structures. By monitoring the temporal variation in the plasmon resonance of the structure, flow-through nanoplasmonic sensing of specific biorecognition events (i.e., detection of the target molecule) can be achieved quickly in a low-volume flow through device. Because hydrogel particles can be used to mask the upper and lower surfaces of the membrane, it is possible to confine capture molecule binding to within the nanopore structures. Exemplary nanoplasmonic biosensors are disclosed in U.S. Patent Publication No. 20120218550 to O'Mahony; and Jonsson et al., "Locally Functionalized Short-range Ordered Nanoplasmonic Pores for Bioanalytical Sensing," *Anal. Chem.* 82(5): 2087-94 (2010), the disclosures of which are incorporated herein by reference in their entirety.

The hydrogel particles can be solid hydrogel polymers or they can be hybrid particles, e.g., a hydrogel coating that surrounds a metal or polymer core (Kim and Lee, "Hydrogel-Coated Gold Nanoparticles," *Polymeric Materials: Science and Engineering* 90: 637-638 (2004); Dingenouts et. al., "Observation of the Volume Transition in Thermosensitive Core-Shell Latex Particles by Small-Angle X-Ray Scattering," *Macromolecules* 31: 8912-8917 (1998), the disclosures of which are incorporated herein by reference in their entirety. Hydrogel particles can be formed as small units of crosslinked monomers.

The hydrogel particle diameter selected for use in the invention will depend, in part, on the nature of the topographical features of the substrate and, thus, the nature of masking desired. The hydrogel particles are preferably, though not necessarily, submicron in diameter. In certain embodiments, the average size of the hydrogel particles is between about 100 nm to about 900 nm, or about 200 nm to about 800 nm in diameter.

The hydrogel particles can be formed of any suitable hydrogel material. Exemplary hydrogel materials include, without limitation, poly-N-isopropylacrylimide (PNIPAM), PNIPAM copolymerized with allyl-iminodiacetic acid, PNIPAM grafted with polyethylene glycol-succinic acid, hydroxypropyl cellulose, or a pullulan acetate/sulfonamide conjugate. Solutions containing the hydrogel particles can be formed using aqueous solutions, including mild buffer solutions, and water. The hydrogel particles can be present in the solution at any suitable concentration that allows for hydrogel particle coverage of the substrate regions devoid of the topographical features. By way of example, the concentration can range from about $10^8$ to about $10^{13}$ particles per milliliter, with a solids weight percentage between about 0.001% to about 1%. This is exemplary, and deviations from these ranges are contemplated. The optimum concentration for uniform coverage depends on extrinsic and intrinsic factors such as the characteristics of the substrate and its topographical features, and the size and area covered by the droplet. For instance, when using a droplet in the picoliter regime, a higher concentration of particles is desirable (e.g., about $10^{11}$ to about $10^{13}$ particles per milliliter).

After selecting the design and substrate for the biosensor device, the structural features of the biosensor device are formed at the one or more sites, and then the coating is applied to the substrate. Coating of the hydrogel particles onto the substrate can be performed using techniques well known in the art. Exemplary coating techniques include, but are not limited to, spraying, spotting, depositing, dip-coating, spin-coating, evaporative lithography, and evaporative deposition of the solution onto the substrate.

Once the hydrogel mask is applied to the substrate, capture molecules can be applied to the substrate whereby the capture molecules bind to or associate with unmasked regions of the substrate, i.e., where the topographical pattern resides.

As used herein, a "capture molecule" is any molecule that is capable of binding to an analyte (i.e. capturing it). Suitable capture molecules include, without limitation, a protein or polypeptide, a nucleic acid molecule, or an organic small molecule probe. It is desirable that the capture molecule binds specifically to the analyte of interest.

Exemplary small molecules include, without limitation: avidin, peptido-mimetic compounds, and vancomycin. One class of peptido-mimetic compounds is disclosed in U.S. patent application Ser. No. 09/568,403 to Miller et al., filed May 10, 2000, the disclosure of which is incorporated herein by reference in its entirety. A preferred peptido-mimetic compound which binds to lipopolysaccharide is a tetratryptophan ter-cyclopentane as disclosed in the above-noted application to Miller et al. Other peptidomimetic compounds can also be employed.

Exemplary polypeptides include, without limitation, a receptor for cell surface molecule or fragment thereof; a lipid A receptor; an antibody or fragment thereof; peptide monobodies of the type disclosed in U.S. patent application Ser. No. 09/096,749 to Koide, filed Jun. 12, 1998, and U.S. patent application Ser. No. 10/006,760 to Koide, filed Nov. 19, 2001, the disclosures of which are incorporated herein by reference in their entirety; a lipopolysacchardide-binding polypeptide; a peptidoglycan-binding polypeptide; a carbohydrate-binding polypeptide; a phosphate-binding polypeptide; a nucleic acid-binding polypeptide; and polypeptides which bind organic warfare agents such as tabun, sarin, soman, GF, VX, mustard agents, botulinum toxin, *Staphylococcus* entertoxin B, and saitotoxin.

Exemplary nucleic acid molecules can be DNA, RNA, or modified nucleic acids that include 2' or 5'-modified sugars, modified nucleotide bases, or peptide-nucleic acids. The nucleic acids can be any length which is suitable to provide specificity for the intended target. Typically, nucleic acids which do not contain modified nucleotides will be at least about 12 to about 100 nucleotides in length. For nucleic acids which contain modified bases, oligonucleotides should be at least about 7 nucleotides in length, up to about 100 nucleotides in length. Nucleic acid capture molecules can be used for Watson-Crick base-pairing with a complementary or partially complementary target nucleic acid molecule depending on the conditions employed (i.e., low stringency, moderate stringency, or high stringency). Alternatively, nucleic acid aptamer molecules can be used for specific binding to other target molecules, typically proteins, carbohydrates, lipids, etc.

The available strategies for attaching the one or more capture molecules include, without limitation, covalently bonding a capture molecule to the surface of the substrate, ionically associating the capture molecule with the surface of the substrate, adsorbing the capture molecule onto the surface of the substrate, or the like. Such association can also include covalently or noncovalently attaching the capture molecule to another moiety (of a coupling agent), which in turn is covalently or non-covalently attached to the surface of the substrate.

In one embodiment, prior to coating the substrate with the hydrogel particles, the substrate surface is treated with a reactant that promotes covalent binding of the one or more capture molecules. This can be achieved by providing a coupling agent precursor and then covalently or non-covalently binding the coupling agent precursor to the surface of the substrate. Once the substrate has been primed with the coupling agent, the capture molecule is exposed to the primed surface under conditions effective to covalently bind to the coupling agent. The binding of the capture molecule to the substrate is carried out under conditions which are effective to allow the one or more target-binding groups thereon to remain available for binding to the target molecule. Suitable coupling agent precursors include, without limitation, silanes functionalized with an epoxide group, a thiol, or an alkenyl.

In a further embodiment, any of the reactant that remains unbound by a capture molecule following the binding is blocked. The blocking agent can be structurally similar to the capture molecules except that they lack a target-binding group or the blocking agents can simply be simple end-capping agents. By way of example, an amino alkyl ester (e.g., glycine methyl ester, glycine ethyl ester, 3-alanine methyl ester, etc.) blocking agent can be introduced to an epoxide-functionalized substrate.

In one embodiment, the one or more capture molecules are directly bound to the substrate surface.

In another embodiment, the one or more capture molecules are attached to the substrate surface via a linker molecule, and the one or more capture molecules and the linker molecule have an affinity-based, non-covalent interaction. For example, the capture molecule and the linker molecule can interact via a streptavidin/biotin interaction or a Protein A/G-immunoglobulin interaction.

Binding of the one or more capture molecules to the one or more sites on the substrate will be carried out in accordance with the selected capture molecules and approaches for attaching the capture molecules to the substrate. In general, this is achieved by exposing the one or more sites to a solution comprising a capture molecule under conditions effective to allow the capture molecule to bind to the site exposed to the solution. This exposure step can be performed using methods well known in the art including, without limitation, printing, spraying, spotting, or depositing the solution onto the substrate or flowing the solution over the substrate at the one or more sites.

After binding of the capture molecules, it is desirable to wash any reactant from the substrate surface and/or blocking any reactant that remains unbound by a capture molecule. This will minimize the likelihood that the target molecule or macromolecular structure can be bound non-specifically to the substrate.

In accordance with one embodiment, two or more sites and two or more capture molecules may be present, with each capture molecule being used at a different site. Thus, the different sites can be prepared using different attachment chemistries (i.e., mutually exclusive) such that a single solution may be used to attach different capture molecules are different sites. Alternatively, the exposure steps can be carried in parallel at distinct sites on the substrate.

In one embodiment, after attaching/binding of the one or more capture molecules the hydrogel particles are removed from the substrate surface. Removal is carried out before exposing the biosensor to a sample for detection of a target molecule. Removal of the hydrogel particles can be achieved by washing the surface of the biosensor with distilled water or a buffer solution. Additionally or alternatively, the hydrogels particles can be removed with sonication. In certain embodiments, even after removing hydrogel particles from the surface, it is desirable for the reasons noted above to wash any reactant from the substrate surface and/or block any reactant that remains unbound by a capture molecule.

In an alternative embodiment, the hydrogel particles are allowed to remain on the substrate surface. Removal is carried out before exposing the biosensor to a sample for detection of a target molecule.

Another aspect relates to a biosensor. The biosensor includes a substrate including a surface having a topographical pattern formed at one or more sites on or in the surface. The substrate can have any of the constructions described above. One or more capture molecules are bound to the one or more sites to form the biosensor, and the one or more capture molecules bind specifically to a target molecule under suitable conditions. The biosensor is unique in that at least 80 percent of one or more types of capture molecules bound to the surface of the substrate are bound at the one or more sites. In other words, less than 20 percent of the one or more types of capture molecules is bound to a region on the surface of the substrate where the capture molecules are not intended.

In one embodiment, at least 85 percent of one or more types of capture molecules bound to the surface of the substrate are bound at the one or more sites. In other words, less than 15 percent of the one or more types of capture molecules is bound to a region on the surface of the substrate where capture molecules are not intended.

In another embodiment, at least 90 percent of one or more types of capture molecules bound to the surface of the substrate are bound at the one or more sites. In other words, less than 10 percent of the one or more types of capture molecules is bound to a region on the surface of the substrate where capture molecules are not intended.

In a further embodiment, at least 95 percent of one or more types of capture molecules bound to the surface of the substrate are bound at the one or more sites. In other words, less than 5 percent of the one or more types of capture molecules is bound to a region on the surface of the substrate where capture molecules are not intended.

In another embodiment, the biosensor exhibits at least an order of magnitude improvement in the limit of detection of the target molecule compared to a biosensor having the one or more capture molecules indiscriminately bound across the entire surface of the substrate.

In certain types of biosensors, the biosensor has an inlet for coupling light into, onto, or across the topographical pattern and an outlet for coupling light that passes from, through, or past the topographical pattern.

The biosensor may also be present in a microfluidic device and exposing the biosensor to the sample involves flowing the sample over the one or more sites on the biosensor surface.

A further aspect relates to a system that includes a biosensor of the type described above, a light source coupled to the biosensor to pass light into or across the topographical pattern, and a detector coupled to the biosensor to detect light passing from or across the topographical pattern.

Figure 1A:
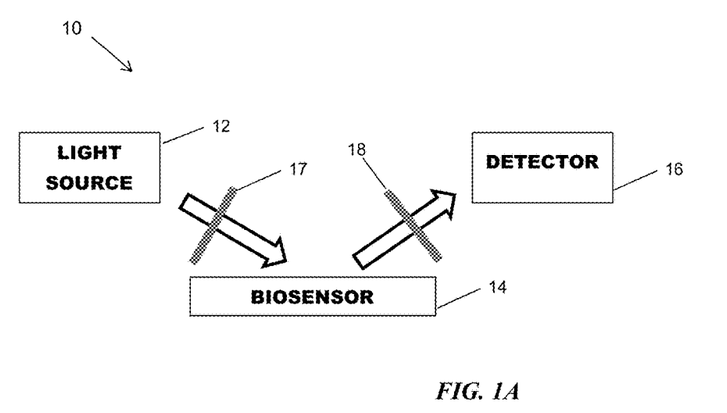
FIG. 1A illustrates a detection system that includes a biosensor, light source, and detector which operate via illumination and detection through an ambient medium (e.g., air or aqueous).

FIG. 1A illustrates one embodiment of the system, where light is directed onto the biosensor substrate through an ambient medium (e.g., air or water) and detected from the biosensor substrate through the ambient medium. The system 10 includes the light source 12, the biosensor 14, and the detector 16.

Figure 1B:
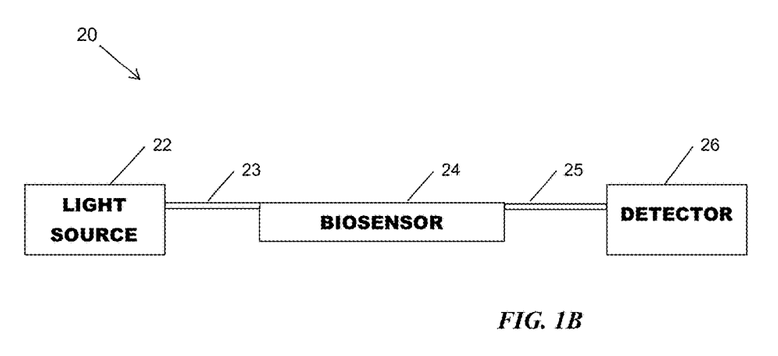
FIG. 1B illustrates a detection system that includes a biosensor, light source, and detector which operate via light coupled into and out of the biosensor via waveguides.

FIG. 1B illustrates another embodiment of the system, where light is coupled into the biosensor via a waveguide and detected from the biosensor via a waveguide. The system 20 includes the light source 22, waveguide 23, biosensor 24, waveguide 25, and detector 26.

The system embodiments illustrated in FIG. 1A-B are exemplary, and are capable of modification to accommodate different biosensor substrates (i.e., different sensing platforms) of the type described above.

The light source functions as a source of illumination and may be, for example, an argon, cadmium, helium, or nitrogen laser and accompanying optics positioned to illuminate the biosensor and the detector. The detector is positioned to capture photoluminescent emissions from the biosensor and to detect changes in photoluminescent emissions from the biosensor. Exemplary detectors include, without limitation, a charge coupled display, spectrophotometer, photodiode array, photomultiplier tube array, or active pixel sensor array.

The system optionally includes a polarizer positioned between the light source and the biosensor. The system also optionally includes a filter positioned between the light source and the biosensor or, alternatively, between the biosensor and the detector. In FIG. 1A, the optional polarizer 17 and filter 18 are shown.

The system may include two or more of the biosensors, each of the biosensors being coupled to the light source and the detector.

A further aspect also relates to a method of detecting the presence of a target molecule in a sample that involves providing a biosensor of the type described above, exposing a sample to the one or more sites on the biosensor surface, and detecting a change in an optical property of biosensor surface at the one or more sites following said exposing.

Samples which can be examined include blood, water, a suspension of solids (e.g., food particles, soil particles, etc.) in an aqueous solution, or a cell suspension from a clinical isolate (such as a tissue homogenate from a mammalian or other patient), cell free extracts, and similar types of suspensions or solutions.

According to this aspect, target molecules may include, without limitation, proteins (including without limitation enzymes, antibodies or fragments thereof), glycoproteins, peptidoglycans, carbohydrates, lipoproteins, a lipoteichoic acid, lipid A, phosphates, nucleic acids which are expressed by certain pathogens (e.g., bacteria, viruses, multicellular fungi, yeasts, protozoans, multicellular parasites, etc.), or organic compounds such as naturally occurring toxins or organic warfare agents, etc. These target molecules can be detected from any source, including food samples, water samples, homogenized tissue from organisms, etc. Moreover, the biological sensor can also be used effectively to detect multiple layers of biomolecular interactions, termed "cascade sensing." Thus, a target, once bound, becomes a probe for a secondary target. This can involve detection of small molecule recognition events that take place relatively far from the substrate's surface.

Presence of the target molecule in the sample will dictate the change in optical property. The specific optical property that is modified will vary depending upon the particular structure used for the biosensor, but generally includes any one or more of transmission peak wavelength shift, absorption peak wavelength shift, or refractive index change. To determine whether a change in optical property has occurred, a baseline optical measurement is made prior to exposure to a sample. After exposure to the sample, a second optical measurement is made and the first and second measurements are compared. Typically any change will depend on the size of the target to be recognized and its concentration within the sample. In another embodiment, the topographical pattern is illuminated with light before and after exposing the sample to the one or more sites on the biosensor surface.

A still further aspect relates to a method of quantifying the amount of a biological target present in a sample. This method includes providing a biosensor of the type described above, exposing a sample to the one or more sites on the biosensor surface, and detecting a change in an optical property of biosensor surface at the one or more sites following said exposing, wherein the amount of biological target is quantifiable based on the extent of the change of the optical property.

To quantify the amount of biological target present in a sample, the light source and the detector can both be present in a spectrometer. A computer with an appropriate microprocessor can be coupled to the detector to receive data from the spectrometer and analyze all the data to compare the optical properties before and after exposure of the biosensor to a target molecule.

EXAMPLES

The following examples are provided to illustrate embodiments of the disclosed methods and devices, but they are by no means intended to limit their scope.

Materials and Methods for Examples 1-5

Photonic Crystal Design. The PhC design used in Example 1-5 has been described before (Pal et al., *Biosens. Bioelectron.* 26:4024-4031 (2011), the disclosure of which is incorporated herein by reference in its entirety). Briefly, the 2D PhC slab structure consists of a 25×26 array of air wells in a triangular lattice pattern with row of wells removed from the center creating a w1 waveguide (line defect). A nanocavity was created by modifying the radius of a single air well adjacent to the waveguide (point defect).

Device Fabrication. A p-type silicon-on-insulator (SOI) wafer (<100>) with a 450 nm silicon device layer on top of 1 µm thick buried silicon oxide (BOX) was used as the starting substrate for the PhCs. For fabrication with PMMA, a 130 nm oxide hard mask was thermally grown on the Si layer via wet oxidization. Polymethylmethacrylate (PMMA) was used as an e-beam resist and a JEOL JBX-9300FS system was used to write the PhC patterns. The pattern was developed and dry etched using argon assisted $CHF_3$ gas in a reactive-ion-etcher to transfer the oxide hard mask, followed by a gas etch with $CF_4$ and $BCl_3$ to etch the Si device layer. The individual PhC devices were cleaved with a diamond scribe to create smooth waveguide facets to facilitate light coupling. For fabrication with HSQ, the native oxide layer of the SOI substrate was stripped using a buffered oxide etch (6:1 hydrofluoric acid/ammonium fluoride). Hydrogen silsesquioxane (HSQ) was used as an e-beam resist and a JEOL JBX-9300FS system was used to write the PhC patterns. After exposure, the pattern was developed and transferred using a $CF_4$ and $BCl_3$ gas etch. The individual PhC devices were cleaved with a diamond scribe to create smooth waveguide facets to facilitate light coupling.

Finite Element Modeling. All solutions were generated using COMSOL Multiphysics (v.4.2a). Bulk diffusion was modeled using the Transport of Diluted Species module. Surface reactions were modeled using General Form Boundary PDEs. Optical Set-up: A tunable laser (Hewlett Packard, model 8168F, output power: −7 to 7 dBm) operating within the wavelength range of 1440-1590 nm (wavelength resolution of 0.02 nm) was used to scan and optically probe the 2D PhC device. A polarization controller was used to excite the TE modes and light was coupled through tapered ridge waveguides into the PhC device using a tapered lensed fiber (Nanonics, Israel). The transmitted optical power was measured using an indium gallium arsenide (InGaAs) photodiode detector (Teledyne Judson Technologies, PA, USA).

Nanoparticle Synthesis. Poly(N-isopropylacrylamide) microgels were prepared via free radical precipitation polymerization. The monomers N-isopropylacrylamide (0.76 g) and bis-acrylamide (BIS) (0.013 g) were dissolved in double distilled water (ddH$_2$O)(50 mL) inside of a 3-neck flask (500 mL). The solution was then mixed with aqueous 1% sodium dodecyl sulphate (SDS) (0.34 mL). The flask containing the solution was equipped with a nitrogen line, overhead stirrer, and gas outlet. The solution was bubbled with nitrogen for 45 minutes to remove dissolved oxygen. The mixture was heated to 60° C. Ammonium persulfate (0.0166 g) was dissolved in ddH$_2$O (0.5 mL) and injected into the flask to start the reaction. The reaction proceeded for 5 hours in an inert atmosphere at a constant stir rate of 200 RPM. After 10 minute the solution became visibly turbid, which was indicative of particle formation. At 5 hours, the flask was removed from heat opened to ambient oxygen while maintaining a constant stir-rate for 15 minutes. The solution was filtered through a 1.2 µm cut-off syringe filter (Millipore). The purified solution was used as is.

Nanoparticle Dipcoating. Both the flat silicon dioxide and nanostructured SOI chips were dipcoated using a syringe pump (Yale Apparatus YA-12) which was modified to hold a pair of tweezers and mounted vertically. The chips were dipped into a 1:100 v/v dilution of PNIPAM particles in ddH$_2$O at a speed of 50 µm per minute until the chip was submerged in solution to approximately half the height of the chip (0.2-0.5 cm, depending on the chip length). The pump was stopped for 30 seconds to allow the chip to equilibrate with the solution before being pulled out at a rate of 100 µm per minute. Once the chips had cleared the water line, the edges of the chip were inspected to ensure they were completely dry before removing them.

Aminosilane-glutaraldehyde Surface Functionalization. To generate a protein-reactive surface, both planar silicon oxide and SOI chips were functionalized with glutaraldehyde (GA) as per the following protocol. First, the chips were carefully cleaned in piranha solution (3:1 (v/v) conc. sulfuric acid to 30% hydrogen peroxide for 30 minutes, followed by ddH$_2$O rinse and dried under a stream of nitrogen gas. Next, the chips were incubated with a 1% (v/v) solution of (3-aminopropyl)dimethylethoxysilane in anhydrous toluene for 20 minutes on an orbital shaker. The chips were then repeatedly washed with anhydrous toluene, dried under a stream of nitrogen and baked at 110° C. for 30 minutes. After the chips had cooled to room temperature (approximately 5 minutes), a solution of 1.25% (v/v) GA in modified PBS buffer (MPBS: 10 mM NaH$_2$PO$_4$, 10 mM Na$_2$HPO$_4$, 150 mM NaCl at pH 7.2) was poured over them, and the chips were left in this solution on a shaker for 60 minutes. Afterwards, they were washed with MPBS and ddH$_2$O and dried under a nitrogen stream.

Antibody Localization on Planar Silicon Oxide Chips. Planar square silicon oxide chips (1 cm×1 cm) were washed in piranha solution and functionalized with GA as described above. The chips were carefully dipcoated with PNIPAM nanoparticles such that half of each chip was passivated while the other half remained protein reactive. Next, the chips were incubated with three different concentrations of rhodamine-labelled IgG (0.1 µm, 0.5 µm and 1 µm) for 60 minutes. Lastly, the chips were washed with MPBS-ET (MPBS buffer with 3 mm Ethylenediaminetetraacetic acid and 0.05% (v/v) Tween-20) for 30 minutes, rinsed with ddH$_2$O and imaged with epifluorescence.

Epifluorescence Microscopy. The fluorescent intensity of the passivated and un-passivated areas of the planar silicon oxide chips was evaluated with an Olympus-BX60 microscope with a Qicam FAST-1394 (Qimaging) active cooled CCD camera. A silicon dioxide chip with no fluorophore was used as a control to measure the background fluorescence. The exposure time was kept constant at 2 seconds. Data analysis was performed with ImageJ (NIH). The relative fluorescence intensity (RFI) was calculated as:

$$RFI = 100 * \left(1 - \frac{(F_M - F_C)}{(F_U - F_C)}\right)$$

where $\overline{F_U}$, $\overline{F_M}$, and $\overline{F_C}$ are the unmasked, masked, and control average fluorescence intensities. The error bars for each condition were computed as the relative fluorescence intensity multiplied by the square root of the sum of the squares of the normalized standard deviations (standard deviation/mean) of the masked and unmasked portions of the chip, and a control chip with no fluorophore:

$$SD_{RFI} = RFI * \sqrt{\left(\frac{SD_{F_U}}{F_U}\right)^2 + \left(\frac{SD_{F_M}}{F_M}\right)^2 + \left(\frac{SD_{F_C}}{F_C}\right)^2}$$

where $SD_{RFI}$ is the calculated error, $SD_{F_U}$, $SD_{F_M}$, and $SD_{F_C}$ are the standard deviations of unmasked, masked, and control fluorescence intensities respectively.

Antibody Localization on PhC Chips. Newly fabricated PhC chips were thermally oxidized in a furnace with an oxygen gas stream at 900° C. for 15 minutes. The chips were then functionalized with aminosilane-glutaraldehyde chemistry. Next, the PhC chips were dipcoated with PNIPAM particles at a rate of 100 μm sec$^{-1}$. After passivation, a 10 μL droplet of 0.1 μm IgG in MPBS buffer was placed on the chip covering the PhC sensing region. The chips were then placed in a humidity chamber for 1 hour (no evaporation appeared to occur), allowing the human-IgG to covalently bind to the exposed GA groups via amine-aldehyde coupling chemistry (Schiff base formation). After antibody immobilization, the remaining aldehyde groups were blocked by incubating the chips in BSA (10 μm) solution in HBS buffer (20 mm2-[4-(2-hydroxyethyl)piperazin-1-yl]ethanesulfonic acid (HEPES), 150 mm NaCl, at pH 7.2) for 1 hour. The chips were then washed with MPBS, dried under nitrogen stream and incubated with a 10 μL droplet of the target solution (anti-IgG) at increasing concentrations diluted in MPBS buffer for a period of 1 hour. Finally, the chips were washed with MPBS-ET for 30 min on an orbital shaker, rinsed with ddH$_2$O and dried under a stream of nitrogen. The chips were then subjected to optical characterization.

Peak Fitting and Data Analysis. After spectra collection, each data set was filtered using Origin (OriginLab, Northampton, Mass.). A fast Fourier transform low-pass filter with a frequency cut-off of 0.5 was used to remove high frequency noise. The peaks were then fit to the Lorentz equation with transmission intensity (a.u.) plotted as a function of wavelength (nm):

$$y = y_0 + \frac{2A}{\pi} * \frac{w}{4(x-x_c)^2 + w^2}$$

The fitted value of $x_c$ (represented in units of wavelength) was used as the location of the minimum absorption for the data-set.

Example 1

Numerical Simulations

Figure 2A:
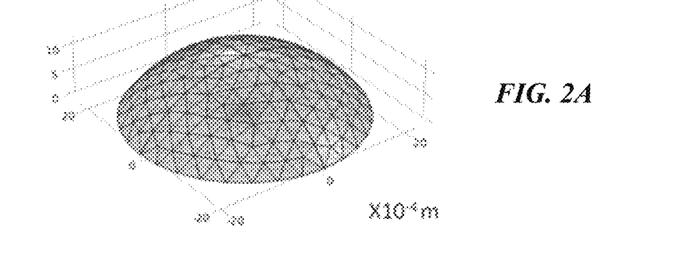
FIGS. 2A-B show geometry and meshing of a droplet with "active" (sensing) and "inactive" (non-sensing) areas for finite element simulations. The surface mesh in FIG. 2A is plotted on a $10^{-4}$ m scale, while the mesh in FIG. 2B is a cross-section of the geometry volume shown on a scale of 0.5 mm.
Figure 2B:
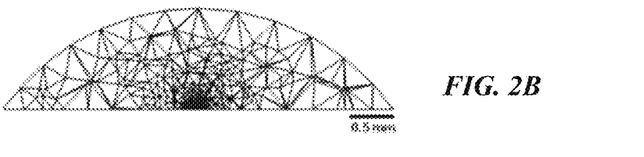

Whether antibody localization to active areas of a nanoscale device will enhance the limit of detection was tested through simulation using finite element methods. The geometry used was a section of a sphere, representing a water droplet with a contact angle of 55 degrees and a volume of approximately 10 μL (FIG. 2A). The flat region of the sectioned sphere was composed of a 70 μm$^2$ area circle (active region) surrounded by a circular contact surface with a 4.5 mm diameter (inactive region). Due to the large size difference between the two areas, a much finer volume (tetrahedral) mesh was required near the active site, which was located at the center of the flat region (FIG. 2B).

The surface reaction was modeled as immunoglobulin gamma (IgG) binding to anti-immunoglobulin gamma (anti-IgG) with 1:1 binding stoichiometry. The surface density of antibody sites was assumed to be a monolayer with a value of $1.2 \times 10^{12}$ antibodies cm$^{-2}$. The $k_{on}$ and $k_{off}$ values were 250 m$^3$s$^{-1}$mol$^{-1}$ and 0.0003 s$^{-1}$, respectively. The diffusion coefficient for IgG was modeled as $5 \times 10^{-11}$ m$^2$ s$^{-1}$. The following diffusion equation was solved for the entire domain:

$$\frac{\partial c}{\partial t} + \nabla \cdot (-D\nabla c) = 0 \quad (1)$$

where c and D are the bulk analyte concentration (mol m$^{-3}$) and diffusion coefficient of the target (m$^2$sec$^{-1}$), respectively. Boundary conditions representing the flux balance between the surface and bulk concentrations of target species were set for the active (sensing) and inactive areas:

$$n \cdot (D\nabla c) = R_{c_s} = -(k_{on}*c*(e*\theta_{max}-c_s)-k_{off}*c_s) \quad (2)$$

where n is a unit vector normal to the reaction surfaces, $R_{cs}$ is the inward flux of the target into the bulk (can be either positive or negative), $k_{on}$ and $k_{off}$ are the kinetic on (m$^3$ sec$^{-1}$mol$^{-1}$) and kinetic off (s$^{-1}$) rate constants for a target and capture-molecule pair, $c_s$ is the surface concentration of bound target (mol m$^{-2}$), $\theta_{max}$, is the maximum surface concentration of available binding sites (mol m$^{-2}$) which was explicitly set at the active and inactive regions, and e is an efficiency factor for antibody localization (dimensionless). The active boundary, representing the "nanoscale sensor" was modeled with an efficiency factor of 1 (e=1) implying that the active region had the maximal surface density of antibodies. The efficiency factor on the inactive boundaries was set to one of three values: e=0 for perfect antibody localization (ABL) (no antibodies at the inactive region), e=0.05 for 95% ABL (surface density of antibody at the inactive region was 5% of the value at the active region), and e=1 for no ABL (the inactive area had the same surface density of antibodies as the active area).

Figures 3A, 3B:
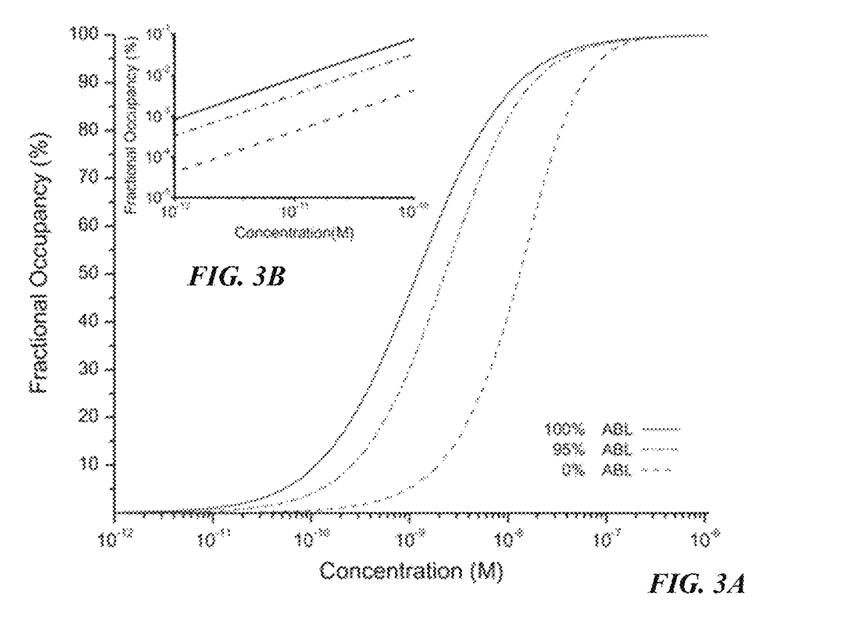
FIG. 3A shows simulated dose-response curves at 100% antibody localization ("ABL") (red solid line), 95% ABL (green dot-dash line), and 0% ABL (blue dashed line).

Dose-response curves (FIG. 3A-B) were generated by plotting fractional occupancy of target, $$\left(\frac{c_s}{\theta_{max}}\right)$$

at the active region for different concentrations of analyte after 24 hours of simulated incubation. The results show a marked difference in the location and shape of the dose-response curve for perfect ABL (e=0), partial ABL (e=0.05), and no ABL (e=1). An assumption of perfect ABL produces a dose-response curve whose midpoint lies at the IgG/anti-IgG equilibrium constant, as expected (at 50% surface coverage, the concentration value matches the expected equilibrium constant, $$K_D = \frac{k_{off}}{k_{on}} = 1.2 \; nM$$

Simulations suggest that even a 95% ABL provides a 10-fold higher surface coverage at the active sensing area relative to the case with no ABL (FIG. 3A). Thus, these simulations predict that ABL with a nanoscale sensor will generate a significantly higher signal compared to a sensor with no ABL at the same analyte concentration, thereby improving the limit of detection.

Example 2

2D Photonic Crystal Biosensor Operation

Figure 4A:
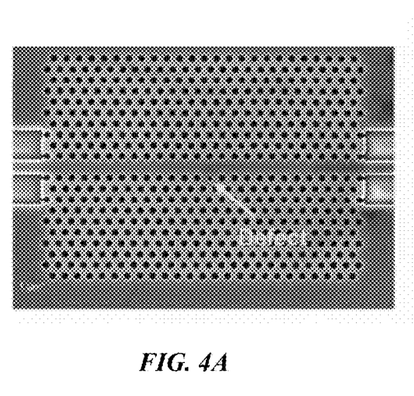
Figure 4B:
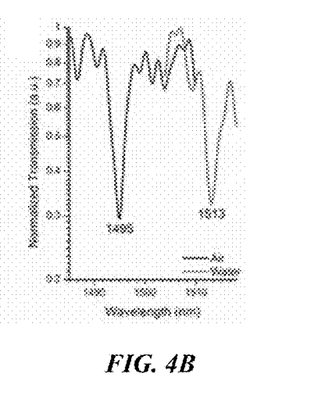

To test these predictions experimentally, a 2-dimensional photonic crystal (2D PhC) biosensor previously employed to detect proteins (Pal et al., *Biosens. Bioelectron.* 44:229-234 (2013), which is hereby incorporated by reference in its entirety) and virus-like particles (Pelton et al., *Colloids Surf.* 20:247-256 (1986), the disclosure of which is incorporated herein by reference in its entirety) was used. The active sensing area of this device is approximately 7 µm by 10 µm and contains of 509 cylindrical wells in silicon with a diameter of 220 nm and a single cylindrical well 150 nm in diameter, with all wells etched to depths of ~400 nm. A w1 waveguide allows propagation of guided modes within the photonic band-gap (PBG) of the crystal. Light is confined within the embedded silicon (Si) layer by total internal reflection from the encasing silicon oxide ($SiO_2$), which has a lower refractive index. Breaking the translational symmetry by modifying the radius of a well to create a defect (FIG. 4A), gives rise to a localized mode within the PBG. Thus, the w1 waveguide photonic crystal allows light transmission at all frequencies except at the resonant defect nano-cavity wavelength, resulting in a characteristic sharp dip in its transmission spectrum. The electric field is strongly confined in the defect at resonance. Analyte binding causes the local refractive index to change resulting in a red-shift of the resonant wavelength due to the strong light-matter interaction within the defect. FIG. 4B depicts the red shifts observed due to the refractive index change when a 2D PhC sensor is analyzed in air (n~1.0) followed by water (n~1.32 at 1550 nm wavelength).

Example 3

Antibody Surface Coverage Evaluation and Localization with PNIPAM Nanoparticle Mask PNIPAM is versatile and can be synthesized as nanoparticles (Andersson et al., *J. Polym. Sci., Part B: Polym. Phys.* 44:3305-3314 (2006), the disclosure of which is incorporated herein by reference in its entirety) with control over their size (Blackburn et al., *Colloid Polym. Sci.* 286:563-569 (2008); Kratz et al., *Colloids Surf.*, 170:137-149 (2000), the disclosures of which are incorporated herein by reference in their entirety) and charge (Hoare et al., *Macromolecules* 37:2544-2550 (2004); Karg et al., *Langmuir* 24:6300-6306 (2008); Tsuji et al., *Langmuir* 21:8439-8442 (2005), the disclosures of which are incorporated herein by reference in their entirety). Several groups have demonstrated that PNIPAM nanoparticles (PNPs) form self-assembled well packed monolayers (Kawaguchi et al., *Colloid Polym. Sci.* 270:53-57 (1992); Pelton et al., *Colloids Surf.* 20:247-256 (1986), the disclosures of which are incorporated herein by reference in their entirety).

Figure 5A:
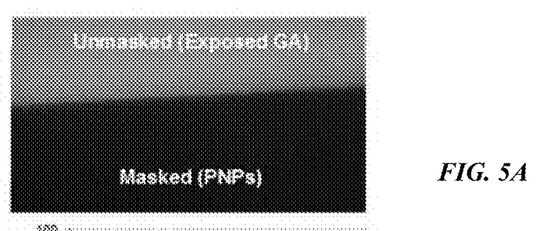
Figure 5B:
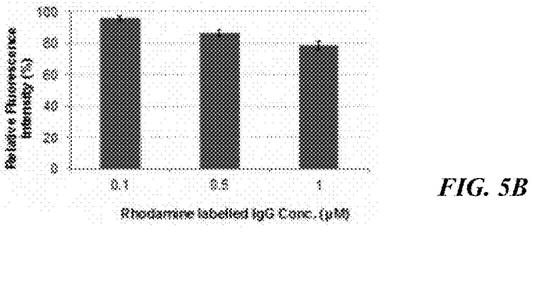

While continuous PNIPAM films have previously been used in surface blocking, a first step was to assess the ability of PNP masks to function in this capacity. This was accomplished using flat silicon dioxide-on-silicon chips, first made protein reactive by aminosilane-gluteraldehyde chemistry followed by dipcoating 315 nm diameter PNIPAM particles on half of the substrate. The entire chip was then exposed to a solution of rhodamine labelled IgG (r-IgG) concentrations and rinsed. The fluorescence intensities of the PNIPAM-masked and unmasked portions of the chip were determined by epifluorescence microscopy, and were visibly higher on the unmasked regions of the substrate (FIG. 5A). The relative fluorescence intensities of the masked regions were found to be 95% lower than the unmasked regions at 0.1 µM r-IgG (FIG. 5B). Higher concentrations had decreased relative fluorescence intensities; however, the nanoparticle masks could still localize antibody effectively within the concentration range likely to be used for sensor functionalization.

Example 4

Nanoparticle Assembly on 2D PhC Structures

Figure 6A:
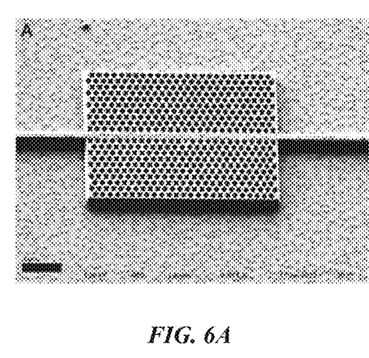
Figure 6B:
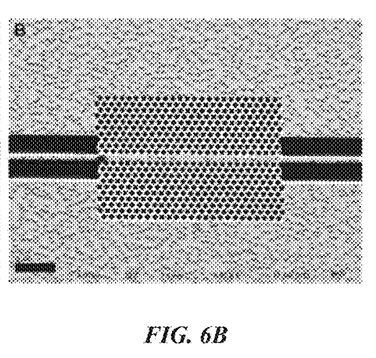

PNPs were deposited on a PhC chip via dip coating. The PNPs preferentially assembled around lithographed features, and did not settle on top of the wells. This behavior was reproducible and consistent on both "extruded" and "embedded" versions of the sensor, fabricated via negative (Hydrogen silsesquioxane (HSQ)) and positive (Polymethylmethacrylate (PMMA)) tone resists respectively with e-beam lithography (FIGS. 6A-B).

Example 5

Enhanced Limit of Detection Via Topographically Selective Passivation

Figure 7A:
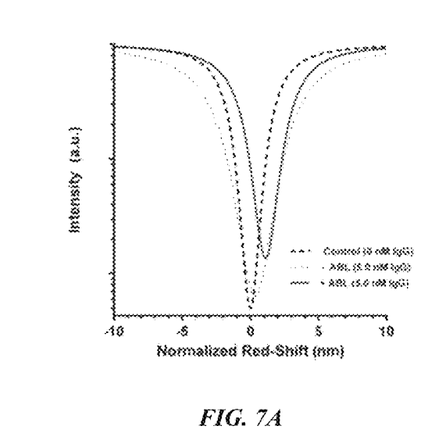
Figure 7B:
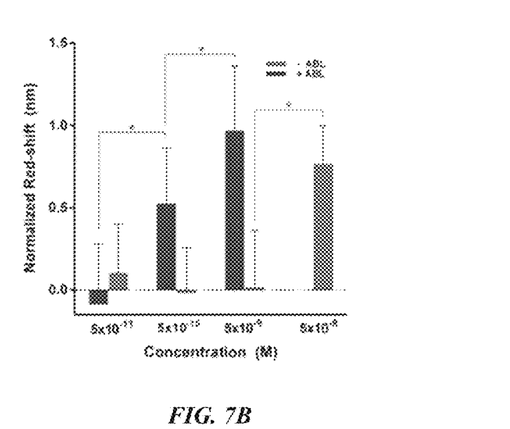

To test the effect of nanoparticle-mediated blocking of non-active portions of the sensor surface during functionalization, 2D PhC chips were functionalized with IgG (probe) and used to detect anti-IgG (target) at various concentrations. The red-shift for each concentration was the difference in the wavelength of the minimum absorption before and after a chip was incubated at that particular anti-IgG concentration, subtracted from the red-shift of an identically functionalized control chip which was not exposed to anti-IgG. Two sets of experiments were run: one in which the chips were unmodified, and another in which the chips were dip-coated with PNIPAM particles prior to probe (IgG) functionalization. Each data point was tested with at least 3 devices. Normalizing the control shift value to zero allowed for a comparison of the relative shift (normalized red-shift) for chips with and without ABL (FIG. 7A). Neither chip had statistically significant shifts from the background with a target concentration of 50 pM. However, the antibody-localized (ABL) chip showed an increasing signal at all higher concentrations of target (FIG. 7B), while it was necessary to test a 10-fold higher concentration of anti-IgG on the non-ABL chip than the highest tested concentration examined on the ABL sensor to see a measurable signal. The lowest detectable concentration of anti-IgG was found to be 0.5 nM with ABL, demonstrating that the LoD of the sensor was improved by at least one order of magnitude.

Discussion of Examples 1-5

To improve the limit of detection of nanoscale biosensors, non-productive loss of target to inactive regions needs to be minimized. Precisely aligning top-down target delivery systems to nanoscale features on a substrate is challenging and requires expensive instrumentation. As an alternative, a fast and inexpensive bottom-up technique was developed based on coating with a monolayer of PNPs. It was demonstrated that these PNPs assemble around topographically distinct features of 2D PhCs, leaving the active sensor area free for immobilization of capture antibodies. Consistent with FEM calculations, this provided over an order of magnitude improvement in the lowest limit of detection for the sensor. It is believed that this strategy will work equally well with other nanoscale sensors, since most have topographical features distinguishing the active sensing area from the remainder of the device.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed:

1. A method of preparing a biosensor comprising:
   providing a substrate comprising a surface having a topographical pattern formed at one or more sites on or in the surface;
   coating the substrate with a solution comprising hydrogel particles, wherein the hydrogel particles self-assemble on the surface to mask the surface except at the one or more sites; and
   binding one or more capture molecules to the one or more sites to form the biosensor.

2. The method according to claim 1 further comprising removing the hydrogel particles from the surface after said binding.

3. The method according to claim 1 wherein the substrate comprises a 2D photonic crystal array, a ring resonator, a toroidal microcavity, a waveguide, a photonic bandgap fiber, a Bragg reflector, a diffraction grating, a plasmonic waveguide, glass-supported gold disk pairs, or a nanoplasmonic pore.

4. The method according to claim 1 wherein the topographical pattern comprises a plurality of pits, pores, or troughs formed in the substrate, a raised structural feature formed on the substrate, or a combination thereof.

5. The method according to claim 1 wherein each of the hydrogel particles comprise poly-N-isopropylacrylimide (PNIPAM), PNIPAM copolymerized with allyl-iminodiacetic acid, PNIPAM grafted with polyethylene glycol-succinic acid, hydroxypropyl cellulose, or a pullulan acetate/sulfonamide conjugate.

6. The method according to claim 1 wherein each of the hydrogel particles comprises a submicron diameter.

7. The method according to claim 1 further comprising, prior to said coating step, treating the substrate surface with a reactant that promotes covalent binding of the one or more capture molecules.

8. The method according to claim 1, wherein said coating step comprises spraying, spotting, depositing, dip-coating, spin-coating, evaporative lithography, or evaporative deposition of the solution onto the substrate.

9. The method according to claim 1, wherein said binding comprises exposing the one or more sites to a solution comprising a capture molecule under conditions effective to allow the capture molecule to bind to the site exposed to the solution.

10. The method according to claim 9, wherein two or more sites and two or more capture molecules are present, each capture molecule being used at a different site.

11. The method according to claim 9, wherein said exposing comprises printing, spraying, spotting, or depositing the solution onto the substrate or flowing the solution over the substrate at the one or more sites.

12. The method according to claim 7 further comprising, after said binding, one or more of:
   washing the reactant from the substrate surface;
   blocking any of said reactant that remains unbound by a capture molecule following said binding; and
   removing hydrogel particles from the substrate surface.

13. The method according to claim 1, wherein the hydrogel particles present in the solution used during said coating are free of the one or more capture molecules.

* * * * *